United States Patent
Zhang et al.

(10) Patent No.: US 11,752,075 B2
(45) Date of Patent: Sep. 12, 2023

(54) ORAL CARE COMPOSITIONS

(71) Applicant: Colgate-Palmolive Company, New York, NY (US)

(72) Inventors: Dennis Zhang, Piscataway, NJ (US); Luciana Rinaudi Marron, Somerset, NJ (US); Stacey Lavender, Chesterfield, NJ (US); Lauren Evans, Highland Park, NJ (US); Neeta Atul Patel, Monmouth Junction, NJ (US); Venda Porter Maloney, Metuchen, NJ (US); Alice Ng, Livingston, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/752,543

(22) Filed: May 24, 2022

(65) Prior Publication Data

US 2022/0387273 A1 Dec. 8, 2022

Related U.S. Application Data

(60) Provisional application No. 63/221,703, filed on Jul. 14, 2021, provisional application No. 63/192,876, filed on May 25, 2021.

(51) Int. Cl.
| | | |
|---|---|---|
| *A61K 8/27* | (2006.01) | |
| *A61K 8/21* | (2006.01) | |
| *A61K 8/46* | (2006.01) | |
| *A61Q 11/00* | (2006.01) | |

(52) U.S. Cl.
CPC ............ *A61K 8/27* (2013.01); *A61K 8/21* (2013.01); *A61K 8/466* (2013.01); *A61Q 11/00* (2013.01)

(58) Field of Classification Search
CPC ........ A61Q 11/00; A61Q 17/005; A61K 8/20; A61K 8/21; A61K 8/25; A61K 9/0053; A61K 2800/28; A61K 2800/412; A61K 2800/51; A61K 2800/805; A61K 2800/87; A61K 2800/92; A61K 8/027; A61K 8/042; A61K 8/19; A61K 8/24; A61K 8/27; A61K 8/345; A61K 8/365; A61K 8/442; A61K 8/466; A61K 8/731; A61K 6/00; A61K 9/00; A61K 9/08; A61K 9/06; A61K 6/15; A61K 33/16; A61K 33/30; A61K 8/30; A61K 8/67
See application file for complete search history.

(56) References Cited

U.S. PATENT DOCUMENTS

| | | |
|---|---|---|
| 9,486,396 B2 | 11/2016 | Jaracz et al. |
| 10,058,493 B2 | 8/2018 | Manus et al. |
| 10,342,750 B2 | 7/2019 | Prencipe et al. |
| 10,441,517 B2 | 10/2019 | Prencipe et al. |
| 10,617,620 B2 | 4/2020 | Prencipe et al. |
| 10,744,077 B2 | 8/2020 | Manus et al. |
| 2009/0202454 A1 | 8/2009 | Mello et al. |
| 2013/0071456 A1 | 3/2013 | Fruge et al. |
| 2015/0313813 A1 | 11/2015 | Rege et al. |
| 2017/0020795 A1 | 1/2017 | Maloney et al. |
| 2017/0348550 A1 | 12/2017 | Josias et al. |
| 2018/0015016 A1 | 1/2018 | Huang et al. |
| 2018/0021234 A1 | 1/2018 | Prencipe et al. |
| 2018/0168961 A1 | 6/2018 | Rege |
| 2018/0207073 A1 | 7/2018 | Poth et al. |
| 2018/0333349 A1* | 11/2018 | Ansari ............... A61K 8/9794 |
| 2019/0038531 A1 | 2/2019 | Rege et al. |
| 2020/0009031 A1 | 1/2020 | Prencipe et al. |
| 2020/0138686 A1* | 5/2020 | Das ..................... A61K 8/19 |
| 2020/0206116 A1 | 7/2020 | Prencipe et al. |
| 2020/0337959 A1 | 10/2020 | Manus et al. |

FOREIGN PATENT DOCUMENTS

CA 2769314 * 2/2011

OTHER PUBLICATIONS

International Search Report and written opinion of the international searching authority issued in international application No. PCT/US2022/030743, dated Oct. 12, 2022.
GLO Science, 2012, Superberry Whitening, Mintel, 1896442.
GLO Science, 2014, One-Night Stand Kit, Mintel, 2849627.
Kao, PureOra, 2021, Whitening Toothpaste, Mintel, 8409581.

* cited by examiner

*Primary Examiner* — Lezah Roberts

(57) ABSTRACT

In one aspect, the present disclosure relates to oral care compositions comprising a source of zinc, a fluoride source, a zwitterionic surfactant and a taurate surfactant. In one aspect the compositions of the disclosure can be used for the treatment or reduction of erosive tooth demineralization, gingivitis, plaque, and dental caries. In one aspect the oral care composition includes zinc citrate, zinc oxide, arginine, cocamidopropyl betaine and at least one taurate surfactant (e.g., sodium methyl cocoyl taurate).

14 Claims, No Drawings

ORAL CARE COMPOSITIONS

CROSS-REFERENCE TO RELATED APPLICATIONS

This application claims the benefit of priority to U.S. Provisional Patent Application Ser. No. 63/192,876, filed May 25, 2021 and U.S. Provisional Patent Application Ser. No. 63/221,703 filed Jul. 14, 2021, the contents of each of which are incorporated herein by reference in their entireties.

FIELD

In one aspect, the present disclosure relates to oral care compositions comprising a source of zinc ion, a fluoride source, a zwitterionic surfactant and a taurate surfactant. In one aspect the compositions of the disclosure can be used for the treatment or reduction of erosive tooth demineralization, gingivitis, plaque, and dental caries. In one aspect the oral care composition comprises zinc citrate, zinc oxide, arginine, cocamidopropyl betaine and at least one taurate surfactant (e.g., sodium methyl cocoyl taurate).

BACKGROUND

Dental erosion involves demineralization and damage to the tooth structure due to acid attack from nonbacterial sources. Erosion occurs on a continuum, initially the acid exposure will soften or demineralize the enamel surface and if unchecked can lead to enamel loss or wear, which can proceed or reach the underlying dentin.

Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization caused by acid produced from the bacterial degradation of fermentable sugar.

Soluble zinc salts, such as zinc citrate, have been used in dentifrice compositions, but have several disadvantages. Zinc ions in solution impart an unpleasant, astringent mouthfeel, so formulations that provide effective levels of zinc, and also have acceptable organoleptic properties, have been difficult to achieve. Moreover, free zinc ions may react with fluoride ions to produce zinc fluoride, which is insoluble and so reduces the availability of both the zinc and the fluoride. Finally, the zinc ions may react with anionic surfactants such as sodium lauryl sulfate, thus interfering with foaming and cleaning.

Sodium lauryl sulfate (SLS) is widely used in dentifrice formulations surfactant. SLS has the benefits, for example, of being neutral with respect to product taste and often does not impact active ingredients stability. However, there has been recent consumer interest in developing various oral care products that do not contain sodium lauryl sulfate. For example, one of the concerns from using SLS has been the potential for skin irritation. However, one of the drawbacks of developing formulations without SLS is that using new surfactant combinations in various oral care compositions (e.g., toothpaste) may lead to product separation because of the change of the ingredients balance in the formula. In some cases a surfactant substitution—e.g., substituting a surfactant for SLS—may potentially have a negative impact on the taste or active ingredients stability. Moreover, microbiological stability of the formulation can be negatively impacted by the absence of sodium lauryl sulfate. There are also production benefits to having SLS in a given formulation. By removing SLS it may lead to a product being aerated during production and it may be more difficult to clean the equipment after the manufacturing process.

Thus, there is a need for providing improved zinc and fluoride containing products for treating or preventing erosion of tooth enamel, that do not contain sodium lauryl sulfate, but nevertheless are still have adequate stability, antimicrobial effectiveness and reduce plaque and treat or control gingivitis as traditional products that contain a sodium lauryl sulfate surfactant.

BRIEF SUMMARY

The Applicants have surprisingly discovered that a zwitterionic surfactant (e.g., a betaine zwitterionic surfactant) (e.g., cocamidopropyl betaine) and a taurate surfactant can be used in certain oral care compositions of the disclosure to replace sodium lauryl sulfate as the primary surfactant. In at least one aspect, it is believed that the combination of a zwitterionic surfactant (e.g., a betaine zwitterionic surfactant) (e.g., cocamidopropyl betaine) and a taurate surfactant, can maintain and possibly improve the efficacy of the oral care compositions disclosed herein. Moreover, in one aspect, the combination of the zwitterionic surfactant and the taurate surfactant is believed to unexpectedly provide enamel repair benefits that are significantly increased relative to oral care compositions comprising a source of zinc ions and sodium lauryl sulfate.

Disclosed herein are oral care compositions comprising:
A source of zinc ion (e.g., zinc citrate and zinc oxide), a fluoride source;
an effective amount of a zwitterionic surfactant (e.g., a betaine zwitterionic surfactant) (e.g., cocamidopropyl betaine); and
an effective amount of a taurate surfactant represented by Formula (1):

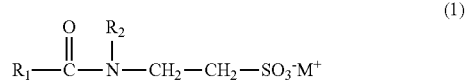

(1)

wherein $R_1$ is a saturated or unsaturated, straight or branched alkyl chain with 6 to 18 C atoms $R_2$ is H or methyl, and $M^+$ is H, sodium, or potassium (e.g., wherein the taurate surfactant is sodium methyl cocoyl taurate).

Methods and uses for this composition are also described throughout. The compositions disclosed herein provide improved repair of acid softened enamel and enhanced antibacterial activity compared to the art. In some embodiments, the source of zinc is added to the dentifrice as a preformed salt. In some embodiments, the oral care composition is a toothpaste or oral gel composition.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight of the entire composition. The amounts given are based on the active weight of the material.

In one aspect, it has been surprisingly found that an oral care composition comprising zinc citrate, zinc oxide, sodium fluoride, arginine, cocamidopropyl betaine and a taurate surfactant (e.g., sodium methyl cocoyl taurate), selected at certain concentrations and amounts, provides improved enamel repair properties when compared to similar oral care formulations that contain an anionic surfactant (e.g., sodium lauryl sulfate or sodium lauryl sarcosinate).

Compositions of the disclosure, e.g., any of Compositions 1.0 et seq, which can include a toothpaste or oral gel, can comprise from 10% to 99% water, by weight of the composition. For example, compositions of the disclosure may comprise at least 10%, 15%, 20%, 25%, 30%, 35% or 40% water, up to a maximum of, for example, 60%, 70%, 80%, 90%, 95% or 99% water, by weight of the composition. As used herein, amounts of water refer to water added directly to the composition, as well as water added as part of ingredients or components which are added as aqueous solutions. In some embodiments, the composition comprises 10-60% water, or 10-50% water, or 10-40% water, or 10-30% water, or 15-30% water, or 20-30% water, or about 25% water, by weight of the composition.

As used herein, the term "preformed salt"—e.g., when used in reference to zinc phosphate—means that the zinc phosphate is not formed in situ in the oral care composition, e.g., through the reaction of phosphoric acid and another zinc salt.

In one aspect, the present disclosure therefore provides an oral care composition (Composition 1.0) wherein the oral care composition comprises:

A source of zinc ions (e.g., zinc citrate and zinc oxide),

A source of fluoride (e.g., sodium fluoride) (e.g., stannous fluoride);

An effective amount of a zwitterionic surfactant (e.g., a betaine zwitterionic surfactant) (e.g., cocamidopropyl betaine); and An effective amount of a taurate surfactant, wherein the taurate surfactant is represented by Formula (1):

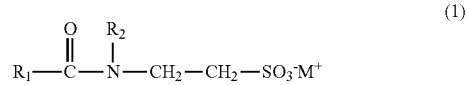

(1)

wherein $R_1$ is a saturated or unsaturated, straight or branched alkyl chain with 6 to 18 C atoms, $R_2$ is H or methyl, and $M^+$ is H, sodium, or potassium (e.g., sodium methyl cocoyl taurate).

For example, Composition 1.0 also includes the following:

1.1 Composition 1.0, wherein the $R_1$ is a saturated or unsaturated, straight or branched alkyl chain with 8 to 14 C atoms.

1.2 Composition 1.0 or 1.1, wherein the taurate surfactant comprises one or more surfactant selected from the group consisting of: potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, and combinations thereof.

1.3 Any of the preceding oral care compositions, wherein the taurate surfactant comprises one or more surfactant selected from the group consisting of: sodium lauroyl methyl taurate (or sodium methyl lauroyl taurate), sodium methyl cocoyl taurate, and combinations thereof.

1.4 Any of the preceding oral care compositions, wherein the taurate surfactant comprises sodium methyl cocoyl taurate (e.g., 0.5%-10% by wt. of sodium methyl cocoyl taurate) (e.g., 1%-5% by wt. of sodium methyl cocoyl taurate) (e.g., about 2.5% by wt. sodium methyl cocoyl taurate).

1.5 Any of the preceding oral care compositions, wherein the taurate surfactant is present in an amount of from 0.25% to 5%, e.g., from 0.4% to 3%, e.g., from 0.4% to 2.75%, e.g., from 0.4% to 2.5%, e.g., from 0.5% to 3%, e.g., from 0.8% to 3%, e.g., from 1% to 3%, e.g., from 1.2% to 2.7%, e.g., from 1.5% to 3%, e.g., from 2% to 3%, e.g., from 1% to 2.8%, e.g., from 1% to 2.7%, e.g., from 1% to 2.5%, e.g., from 1.5% to 2.8%, e.g., from 1.5% to 2.5%, e.g., from 1.8% to 3%, e.g., from 1.8% to 2.8%, e.g., from 1.8% to 2.7%, e.g., from 1.8% to 2.5%, e.g., about 2.5% by weight of the composition.

1.6 Any of the preceding oral care compositions, wherein the taurate surfactant comprises sodium methyl cocoyl taurate in an amount from 0.25%-5% by wt. of the total composition (e.g., about 2.5% by wt. of the total composition).

1.7 Any preceding oral care composition, wherein the amount of the fluoride source is in an amount from 0.01% to 5% by weight, relative to the weight of the oral care composition, for example, from 0.05 to 4% by weight, or from 0.1% to 3% by weight, or from 0.2 to 2% by weight, or from 0.3 to 1% by weight, or from 0.3 to 0.5% by weight, or about 0.32% by weight (e.g., 0.32% by weight).

1.8 Any of the preceding oral care compositions, wherein the fluoride source is selected from the group consisting of: sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluorides and combinations thereof.

1.9 The preceding oral care composition, wherein the fluoride ion source comprises sodium fluoride (e.g., from 0.2%-2% by wt. of sodium fluoride) (e.g., about 0.32% by wt.).

1.10 The composition of 1.9, wherein the fluoride ion source comprises stannous fluoride (e.g., from 0.2%-2% by wt. of stannous fluoride) (e.g., about 0.45%).

1.11 The composition of 1.9, wherein the fluoride ion source comprises sodium monofluorophosphate (e.g., from 0.2%-2% by wt. of sodium monofluorophosphate).

1.12 Any preceding oral care composition, wherein the composition comprises water in the amount of 5% by weight or more (e.g., 10% by weight or more), relative to the weight of the oral care composition, for example, 10-90%, or 10-80%, or 10-70%, or 10-60%, or 10-50%, or 10-40%, or 10-30%, or 15-30%, 15%-40% 20%-40%, 20-35%, or 20-50%, or 30-35%, or about 25% or about 30%, or about 32% by weight of the composition.

1.13 Any preceding oral care composition, further comprising an organic buffer system, wherein the buffer system comprises a carboxylic acid and one or more conjugate base salts thereof, for example, alkali metal salts thereof (e.g., citric acid and sodium citrate).

1.14 Any preceding oral care composition, wherein the composition comprises the organic acid buffer system in an amount of 0.1 to 5.0% by weight of the composition, measured as the combined amount of organic acid and any conjugate base salts (e.g., citric acid and sodium citrate); for example, from 0.5 to 4.0%, or from 1.0 to 3.0%, or from 1.5 to 3.0%, or from 1.0 to 2.4%, or from 1.0% to 2.0%, or from 1.0% to 1.5%, or about 1.2%, by weight of the composition.

1.15 Any preceding oral care composition, wherein the oral care composition further comprises an abrasive, for example, silica abrasives, calcium abrasives, and other abrasives as disclosed herein.

1.16 Any preceding oral care composition, further comprising one or more humectants, as described herein, e.g., selected from sorbitol, glycerol, xylitol and propylene glycol, or combinations thereof, e.g., a combination of sorbitol and glycerin.

1.17 Any of the preceding oral care compositions, wherein the zwitterionic surfactant comprises cocamidopropyl betaine, (e.g., in an amount of 0.5-5% by weight of the total composition) (e.g., 3% by wt. of the total composition).

1.18 Any preceding oral care composition, further comprising an effective amount of one or more alkali phosphate salts for example orthophosphates, pyrophosphates, tripolyphosphates, tetraphosphates or higher polyphosphates.

1.19 Composition 1.18, wherein the alkali phosphate salts comprise tetrasodium pyrophosphate and/or tetrapotassium pyrophosphate, for example, in an amount of 0.25 to 5% by weight of the composition, e.g., from 0.25%-1% by wt., or from 0.25%-0.75% by wt., or about 0.5% by wt., or from 1-4% by wt., or from 2-4% by wt., or from 1-2% by wt., or about 1.5% by wt., or about 2% or about 4%, by weight.

1.20 Composition 1.18 or 1.19, wherein the alkali phosphate salts comprise sodium tripolyphosphate or potassium tripolyphosphate, for example, in an amount of 0.5 to 6% by weight of the composition, e.g., 1-4%, or 2-3% or about 3% by weight.

1.21 Any preceding oral care composition, further comprising a whitening agent.

1.22 Any preceding oral care composition, wherein the source of zinc ions comprises a zinc salt selected from zinc citrate, zinc oxide, zinc lactate, zinc pyrophosphate, zinc sulfate, zinc phosphate, zinc chloride and combinations thereof.

1.23 The preceding oral care composition, wherein the source of zinc ion comprises zinc oxide and zinc citrate.

1.24 Composition of 1.23, wherein the ratio of the amount of zinc oxide (e.g., wt. %) to zinc citrate (e.g., wt. %) is from 1.5:1 to 4.5:1 (e.g., 2:1, 2.5:1, 3:1, 3.5:1, or 4:1).

1.25 Any of composition 1.23 or 1.24, wherein the zinc citrate is in an amount of from 0.25% to 1.0% by wt. (e.g., 0.5% by wt.) and zinc oxide may be present in an amount of from 0.75% to 1.25% by wt. (e.g., 1.0% by wt.) based on the weight of the oral care composition.

1.26 Any of composition 1.22-1.25, wherein zinc citrate is present in an amount of about 0.5% by wt.

1.27 Any of composition 1.22-1.26, wherein the zinc oxide is present in an amount of about 1.0% by wt.

1.28 Any of composition 1.22-1.27, wherein the zinc citrate is present in an amount of about 0.5% by wt. and the zinc oxide is present in an amount of about 1.0% by wt.

1.29 Any of the preceding oral care compositions, wherein the source of zinc ions comprises zinc phosphate.

1.30 The preceding oral care composition, wherein the zinc phosphate is added as a pre-formed salt.

1.31 Any preceding oral care composition, wherein the oral care composition is selected from: a dentifrice (e.g., a toothpaste or oral gel), powder (e.g., tooth powder), cream, mouthwash, mousse, foam, lozenge, oral tablet, mouth spray, strip, or gum (e.g., chewing gum).

1.32 Any preceding oral care composition, wherein the pH of the composition is from 6 to 9, such as from 6.5 to 8, or from 6.5 to 7.5, or about 7.0.

1.33 Any preceding oral care composition, wherein the composition is a single-phase composition (e.g., not a dual-phase composition).

1.34 Any preceding oral care composition, wherein the composition is essentially free or free of phosphates of more than four phosphate groups.

1.35 Any preceding oral care composition, wherein the composition is essentially free or free of phosphates of more than three phosphate groups.

1.36 Any preceding oral care composition, wherein the composition is essentially free or free of hexametaphosphate salts (e.g., sodium hexametaphosphate).

1.37 Any of the preceding oral care compositions, wherein the composition is effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.38 Any preceding oral care compositions, wherein the composition further comprises a polymer selected from the group consisting of: carboxymethyl cellulose (free form or a salt, e.g., sodium salt), a gum (e.g., xanthan gum, carrageenan gum, or gum arabic), polyethylene glycol (e.g., polyethylene glycol 200, 400, 600 or 800, or a mixture thereof), and combinations thereof, for example, a mixture of sodium carboxy methyl cellulose and xanthan gum.

1.39 Composition 1.38, wherein the polymer comprises sodium carboxy methyl cellulose (e.g., from 0.25%-2% by wt. of the total composition).

1.40 Composition 1.38, wherein the polymer comprises xanthan gum and/or sodium carboxy methyl cellulose (e.g., from 0.1%-2% by wt. of the total composition).

1.41 Any preceding oral care composition further comprising a silica thickener and/or a silica abrasive.

1.42 Any preceding oral care composition, wherein the oral care composition comprises an anionic surfactant that is not sodium lauryl sulfate, wherein the anionic surfactant is selected from the group consisting of: water-soluble salts of higher fatty acid monoglyceride monosulfates (such as the sodium salt of the monosulfated monoglyceride of hydrogenated coconut oil fatty acids), sodium cocomonoglyceride sulfate, higher alkyl-ether sulfates (e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$), higher alkyl aryl sulfonates such as sodium dodecyl benzene sulfonate (sodium lauryl benzene sulfonate), higher alkyl sulfoacetates (such as sodium lauryl sulfoacetate (dodecyl sodium sulfoacetate)), higher fatty acid esters of 1,2 dihydroxy propane sulfonate, sulfocolaurate (N-2-ethyl laurate potassium sulfoacetamide) and sodium lauryl sarcosinate, e.g., wherein the anionic surfactant that is not sodium lauryl sulfate is present in an amount from 0.5%-10% by wt. of the composition.

1.43 Any of the preceding oral care compositions composition comprising an amino acid.

1.44 Any of the preceding oral care compositions wherein the amino acid is a basic amino acid (e.g., arginine).

1.45 Any of the preceding oral care compositions wherein the amino acid is a basic amino acid provided in the form of a di- or tri-peptide comprising arginine or lysine, or salts thereof.

1.46 Any of the preceding oral care compositions wherein the basic amino acid comprises arginine or lysine, and wherein the arginine or lysine is present in an amount corresponding to 1% to 15%, e.g., 3 wt. % to 10 wt. % of the total composition weight, about e.g., 1.5%, 4%, 5%, or 8%, wherein the weight of the basic amino acid is calculated as free form.

1.47 Any of the preceding oral care compositions wherein the amino acid comprises arginine from 0.1 wt. %-6.0 wt. % (e.g., about 1.5 wt. %) (e.g., about 5 wt. %) of the total composition, wherein the weight of the arginine is calculated as free form.

1.48 Any of the preceding oral care compositions wherein the amino acid is arginine about 1.5 wt. of the total composition, wherein the weight of the arginine is calculated as free form.

1.49 Any of the preceding oral care compositions wherein the amino acid is arginine from 4.5 wt. %-8.5 wt. % (e.g., about 5.0 wt. %) of the total composition, wherein the weight of the basic amino acid is calculated as free form.

1.50 Any of the preceding oral care compositions wherein the amino acid is arginine about 5.0 wt. % of the total composition, wherein the weight of the basic amino acid is calculated as free form.

1.51 Any of the preceding oral care compositions wherein the amino acid is arginine from 3.5 wt. %-9 wt. % of the total composition, wherein the weight of the basic amino acid is calculated as free form.

1.52 Any of the preceding oral care compositions wherein the amino acid is L-arginine.

1.53 Any of the preceding oral care compositions wherein the amino acid is a free form arginine.

1.54 Any of the preceding oral care compositions wherein the amino acid is arginine or lysine in partially or wholly in salt form.

1.55 Composition 1.54 wherein the amino acid is arginine phosphate.

1.56 Composition 1.54 wherein the amino acid is arginine hydrochloride.

1.57 Composition 1.54 wherein the amino acid is arginine bicarbonate.

1.58 Any of the preceding oral care compositions wherein the amino acid is arginine or lysine ionized by neutralization with an acid or a salt of an acid.

1.59 Any of the foregoing compositions, wherein the zwitterionic surfactant is a betaine zwitterionic surfactant (e.g., from 0.1%-5% by wt. of the total composition) (e.g., 0.5%-4% by wt. of the total composition) (e.g., about 0.9% by wt. of the total composition) (e.g., about 3% by wt. of the total composition).

1.60 The preceding oral care composition, wherein the betaine zwitterionic surfactant is a C8-C16 aminopropyl betaine (e.g., cocamidopropyl betaine)

1.61 The preceding oral care composition wherein the C8-C16 aminopropyl betaine is cocamidopropyl betaine.

1.62 Any of the preceding oral care compositions, wherein the oral care composition comprises cocamidopropyl betaine, and wherein the cocamidopropyl betaine is present in an amount of from 0.5% to 5% by wt. of the total composition (e.g., about 0.9% by wt.) (e.g., about 3% by wt.).

1.63 The preceding oral care composition, wherein the cocamidopropyl betaine is from 0.5% to 4% by wt. % of the total composition (e.g., about 0.9% by wt. of the total composition) (e.g., about 3% by wt. of the total composition).

1.64 The preceding oral care composition wherein the cocamidopropyl betaine is from 0.5% to 3.5% (e.g., from 0.75%-1.5% by wt.) (e.g., about 0.9% by wt. of the total composition) (e.g., about 3% by wt. of the total composition).

1.65 The preceding oral care composition wherein the cocamidopropyl betaine is from 0.75% to 3.5% (e.g., from 0.75%-1.25% by wt.) (e.g., about 0.9% by wt. of the total composition) (e.g., about 3% by wt. of the total composition).

1.66 Any of the preceding oral care compositions wherein the composition comprises cocamidopropyl betaine and sodium methyl cocoyl taurate in a wt. % ratio of (e.g., wt. %) is from 3:1 to 0.5:1 (e.g., 2:1, 1.5:1, 1.2:1, or 1:1)

1.67 Any preceding oral care composition, wherein the oral care composition is free of sodium lauryl sulfate.

1.68 Any preceding oral care composition, wherein the composition comprises:
Zinc phosphate;
Stannous fluoride;
Sodium methyl cocoyl taurate;
Cocamidopropyl Betaine and
An orally acceptable carrier.

1.69 Any preceding oral care composition, wherein the composition comprises:
Zinc oxide;
Zinc citrate;
Sodium fluoride or Sodium monofluorophosphate or Stannous Fluoride;
Sodium methyl cocoyl taurate;
Cocamidopropyl Betaine and
An orally acceptable carrier.

1.70 Any preceding oral care composition, wherein the composition comprises:
Zinc oxide;
Zinc citrate;
Arginine;
Sodium fluoride or Sodium monofluorophosphate;
Sodium methyl cocoyl taurate;
Cocamidopropyl Betaine and
An orally acceptable carrier.

1.71 Any preceding oral care composition, wherein the composition comprises:
Zinc phosphate from 0.5-4% by wt.;
Stannous fluoride 0.2%-2% by wt.;
Sodium methyl cocoyl taurate from 0.5%-4% by wt.;
Cocamidopropyl Betaine from 0.5%-5% by wt.; and
An orally acceptable carrier.

1.72 Any preceding oral care composition, wherein the composition comprises:
Zinc oxide from 0.5%-1.5% (e.g., 1% by wt.);
Zinc citrate from 0.25%-0.75% (e.g., 0.5% by wt.);
Sodium fluoride or Sodium monofluorophosphate (e.g., from 0.2%-2% by wt.);
Sodium methyl cocoyl taurate from 0.5%-4% by wt. (e.g., about 2.5% by wt.);
Cocamidopropyl Betaine from 0.5%-5% by wt. (e.g., 3% by wt.) (e.g., about 0.9% by wt.); and
An orally acceptable carrier.

1.73 Any preceding oral care composition, wherein the composition comprises:
Zinc oxide from 0.5%-1.5% (e.g., 1% by wt.);
Zinc citrate from 0.25%-0.75% (e.g., 0.5% by wt.);
Arginine from 0.5%-7% by wt. (e.g., 1.5% by wt.) (e.g., about 5% by wt.), wherein the amount of arginine is calculated as free form;
Sodium fluoride or Sodium monofluorophosphate;
Sodium methyl cocoyl taurate from 0.5%-4% by wt. (e.g., about 2.5% by wt.);
Cocamidopropyl Betaine from 0.5%-5% by wt. (e.g., 3% by wt.) (e.g., about 0.9% by wt.); and
An orally acceptable carrier.

1.74 Any preceding oral care composition comprising the following ingredients:

| Ingredient Ingredients | % by wt. of total composition Weight % |
|---|---|
| Water | Q.S. (e.g., 15%-40%) |
| Humectants | 15%-50% (e.g., 35%) |
| Polymers | 0.5%-5% (e.g., 1.4%) |
| Abrasives | 10%-25% (e.g., 15%) |
| Thickeners | 1%-10% (e.g., about 6%) |
| Zinc Citrate | 0.1%-5% (e.g., 0.5%) |
| Zinc Oxide | 0.1%-5% (e.g., 1%) |
| L-Arginine | 0.1-5 (e.g., 1.5) |
| Flavor, Sweetener, Colors | 1-5% (e.g., 2.5%) |
| Alkali Phosphate Salts | 0.1%-2% (e.g., 0.5%) |
| Sodium Methyl Cocoyl Taurate | 0.01-10 (e.g., 2.5%) |
| Cocamidopropyl Betaine 30% solution | 0.1-5 (e.g., 3%) |
| Sodium Fluoride | 0.1%-0.8% (e.g., 0.32%) |
| Preservative | 0.1%-1% (e.g., 0.4%) |
| 85% Syrupy Phosphoric Acid | 0.1%-1% (e.g., 0.35%) |
| Total Components | 100.0% |

1.75 Any preceding oral care composition wherein the composition does not contain any sodium lauryl sulfate.

1.76 Any of composition from 1.0-1.74, wherein the composition is substantially free of sodium lauryl sulfate.

1.77 Any preceding oral care composition, wherein the oral care composition is in the form selected from: a dentifrice (e.g., a toothpaste or oral gel), powder (e.g., tooth powder), cream, mouthwash, mousse, foam, mouth spray, oral tablet, strip, or gum (e.g., chewing gum).

1.78 Any of the preceding oral care compositions further comprising a preservative selected from: benzyl alcohol, Methylisothizolinone ("MIT"), Sodium bicarbonate, lauryl alcohol, and polyphosphate.

1.79 Any of the preceding oral care compositions comprising nitric acid or a water-soluble nitrate salt (e.g., potassium nitrate).

1.80 The preceding oral care composition, wherein the water-soluble nitrate salt is selected from an alkali or alkaline earth metal nitrate, or zinc nitrate, silver nitrate, or ammonium nitrate.

1.81 The preceding oral care composition, wherein the water-soluble nitrate salt is an alkali metal nitrate salt or an alkaline earth metal nitrate salt.

1.82 The preceding oral care composition, wherein the nitrate salt is selected from lithium nitrate, sodium nitrate, potassium nitrate, magnesium nitrate, and calcium nitrate.

1.83 The preceding oral care composition, wherein the nitrate salt is potassium nitrate.

1.84 Any preceding oral care composition, wherein the oral care composition is free or substantially free of sodium lauryl sulfate.

1.85 Any of the preceding oral care compositions, wherein the oral care composition comprises hyaluronic acid (e.g., high-molecular weight hyaluronic acid (HA)) or an sodium hyaluronate (e.g., average MW>100,000 Da, e.g., 300 kDa-1 MDa).

1.86 Any preceding oral care composition, wherein the oral care composition does not contain any sodium lauryl sulfate.

1.87 Any preceding oral care composition, wherein the composition comprises:
Zinc oxide 0.5%-1.5% (e.g., 1% by wt.);
Zinc citrate 0.25%-0.75% (e.g., 0.5% by wt.);

Sodium fluoride or Sodium monofluorophosphate;
Sodium methyl cocoyl taurate 0.5%-4% by wt. (e.g., about 2.5% by wt.);
Cocamidopropyl Betaine 0.5%-5% by wt. (e.g., 3% by wt.) (e.g., about 2.1%) (e.g., about 0.9% by wt.); and
Wherein the composition does not contain any sodium lauryl sulfate.

In one aspect, the compositions of the disclosure include Composition 2.0, wherein Composition 2.0 comprises:
A source of zinc ions (e.g., zinc citrate and zinc oxide),
A source of fluoride (e.g., sodium fluoride) (e.g., stannous fluoride);
An effective amount of a taurate surfactant, wherein the taurate surfactant is represented by Formula (1):

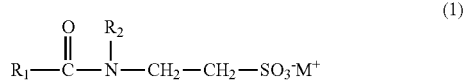

$$R_1-\overset{O}{\underset{\|}{C}}-\overset{R_2}{\underset{|}{N}}-CH_2-CH_2-SO_3^-M^+ \quad (1)$$

wherein $R_1$ is a saturated or unsaturated, straight or branched alkyl chain with 6 to 18 C atoms, $R_2$ is H or methyl, and $M^+$ is H, sodium, or potassium (e.g., sodium methyl cocoyl taurate); and
wherein the composition does not contain any sodium lauryl sulfate.

For example, Composition 2.0 also includes the following:

2.1 Composition 2.0, wherein the $R_1$ is a saturated or unsaturated, straight or branched alkyl chain with 8 to 14 C atoms.

2.2 Composition 2.0 or 2.1, wherein the taurate surfactant comprises one or more surfactant selected from the group consisting of: potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, and combinations thereof.

2.3 Any of the preceding oral care compositions, wherein the taurate surfactant comprises one or more surfactant selected from the group consisting of: sodium lauroyl methyl taurate (or sodium methyl lauroyl taurate), sodium methyl cocoyl taurate, and combinations thereof.

2.4 Any of the preceding oral care compositions, wherein the taurate surfactant comprises sodium methyl cocoyl taurate (e.g., 0.5%-10% by wt. of sodium methyl cocoyl taurate) (e.g., 1%-5% by wt. of sodium methyl cocoyl taurate) (e.g., about 2.5% by wt. sodium methyl cocoyl taurate).

2.5 Any of the preceding oral care compositions, wherein the taurate surfactant is present in an amount of from 0.25% to 5%, e.g., from 0.4% to 3%, e.g., from 0.4% to 2.75%, e.g., from 0.4% to 2.5%, e.g., from 0.5% to 3%, e.g., from 0.8% to 3%, e.g., from 1% to 3%, e.g., from 1.2% to 2.7%, e.g., from 1.5% to 3%, e.g., from 2% to 3%, e.g., from 1% to 2.8%, e.g., from 1% to 2.7%, e.g., from 1% to 2.5%, e.g., from 1.5% to 2.8%, e.g., from 1.5% to 2.5%, e.g., from 1.8% to 3%, e.g., from 1.8% to 2.8%, e.g., from 1.8% to 2.7%, e.g., from 1.8% to 2.5%, e.g., about 2.5% by weight of the composition.

2.6 Any of the preceding oral care compositions, wherein the taurate surfactant comprises sodium methyl cocoyl taurate in an amount from 0.25%-5% by wt. of the total composition (e.g., about 2.5% by wt. of the total composition).

2.7 Any preceding oral care composition, wherein the amount of the fluoride source is in an amount from 0.01% to 5% by weight, relative to the weight of the oral care composition, for example, from 0.05 to 4% by weight, or from 0.1% to 3% by weight, or from 0.2 to 2% by weight, or from 0.3 to 1% by weight, or from 0.3 to 0.5% by weight, or about 0.32% by weight (e.g., 0.32% by weight).

2.8 Any of the preceding oral care compositions, wherein the fluoride source is selected from the group consisting of: sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluorides, and combinations thereof.

2.9 The preceding oral care composition, wherein the fluoride ion source comprises sodium fluoride (e.g., from 0.2%-2% by wt. of sodium fluoride) (e.g., about 0.32% by wt.).

2.10 The composition of 2.9, wherein the fluoride ion source comprises stannous fluoride (e.g., from 0.2%-2% by wt. of stannous fluoride) (e.g., about 0.45%).

2.11 The composition of 2.9, wherein the fluoride ion source comprises sodium monofluorophosphate (e.g., from 0.2%-2% by wt. of sodium monofluorophosphate).

2.12 Any preceding oral care composition, wherein the composition comprises water in the amount of 5% by weight or more (e.g., 10% by weight or more), relative to the weight of the oral care composition, for example, 10-90%, or 10-80%, or 10-70%, or 10-60%, or 10-50%, or 10-40%, or 10-30%, or 15-30%, 15%-40% 20%-40%, 20-35%, or 20-50%, or 30-35%, or about 25% or about 30%, or about 32% by weight of the composition.

2.13 Any preceding oral care composition, wherein the source of zinc ions comprises a zinc salt selected from zinc citrate, zinc oxide, zinc lactate, zinc pyrophosphate, zinc sulfate, zinc phosphate, zinc chloride, and combinations thereof.

2.14 The preceding oral care composition, wherein the source of zinc ion comprises zinc oxide and zinc citrate.

2.15 Composition of 2.14, wherein the ratio of the amount of zinc oxide (e.g., wt. %) to zinc citrate (e.g., wt. %) is from 1.5:1 to 4.5:1 (e.g., 2:1, 2.5:1, 3:1, 3.5:1, or 4:1).

2.16 Any of composition 2.14 or 2.15, wherein the zinc citrate is in an amount of from 0.25% to 1.0% by wt. (e.g., 0.5% by wt.) and zinc oxide may be present in an amount of from 0.75% to 1.25% by wt. (e.g., 1.0% by wt.) based on the weight of the oral care composition.

2.17 Any of composition 2.14-2.16, wherein zinc citrate is present in an amount of about 0.5% by wt.

2.18 Any of composition 2.14-2.17, wherein the zinc oxide is about 1.0% by wt.

2.19 Any of composition 2.14-2.18, wherein the zinc citrate is about 0.5% by wt. and the zinc oxide is about 1.0% by wt.

2.20 Any of the preceding oral care compositions, wherein the source of zinc ions comprises zinc phosphate.

2.21 The preceding oral care composition, wherein the zinc phosphate is added as a pre-formed salt.

2.22 Any preceding oral care composition, wherein the oral care composition is in the form selected from: a dentifrice (e.g., a toothpaste or oral gel), powder (e.g., tooth powder), mousse, foam, cream, mouthwash, oral table, lozenge, strip, or gum (e.g., chewing gum).

2.23 Any of the foregoing compositions, wherein the zwitterionic surfactant is a betaine zwitterionic surfactant (e.g., from 0.1%-5% by wt. of the total composition) (e.g., 0.5%-4% by wt. of the total composition) (e.g., about 0.9% by wt. of the total composition) (e.g., about 3% by wt. of the total composition).

2.24 The preceding oral care composition, wherein the betaine zwitterionic surfactant is a C8-C16 aminopropyl betaine (e.g., cocamidopropyl betaine)

2.25 The preceding oral care composition wherein the C8-C16 aminopropyl betaine is cocamidopropyl betaine.

2.26 Any of the preceding oral care compositions, wherein the oral care composition comprises cocamidopropyl betaine, and wherein the cocamidopropyl betaine is present in an amount of from 0.5% to 5% by wt. of the total composition (e.g., about 0.9% by wt.) (e.g., about 3% by wt.).

2.27 The preceding oral care composition, wherein the cocamidopropyl betaine is from 0.5% to 4% by wt. % of the total composition (e.g., about 0.9% by wt. of the total composition) (e.g., about 3% by wt. of the total composition).

2.28 The preceding oral care composition wherein the cocamidopropyl betaine is from 0.5% to 3.5% (e.g., from 0.75%-1.5% by wt.) (e.g., about 0.9% by wt. of the total composition) (e.g., about 3% by wt. of the total composition).

2.29 The preceding oral care composition wherein the cocamidopropyl betaine is from 0.75% to 3.5% (e.g., from 0.75%-1.25% by wt.) (e.g., about 0.9% by wt. of the total composition) (e.g., about 3% by wt. of the total composition).

2.30 Any of the preceding oral care compositions wherein the composition comprises cocamidopropyl betaine and sodium methyl cocoyl taurate in a wt. % ratio of (e.g., wt. %) is from 3:1 to 0.5:1 (e.g., 2:1, 1.5:1, 1.2:1, or 1:1)

2.31 Any preceding oral care composition, wherein the composition comprises:
Zinc phosphate;
Stannous fluoride;
Sodium methyl cocoyl taurate;
An orally acceptable carrier; and
wherein the oral care composition is free of sodium lauryl sulfate.

2.32 Any preceding oral care composition, wherein the composition comprises:
Zinc oxide;
Zinc citrate;
Sodium fluoride or Sodium monofluorophosphate or Stannous Fluoride;
Sodium methyl cocoyl taurate;
An orally acceptable carrier; and
wherein the oral care composition is free of sodium lauryl sulfate.

2.33 Any preceding oral care composition, wherein the composition comprises:
Zinc oxide;
Zinc citrate;
Arginine;
Sodium fluoride or Sodium monofluorophosphate;
Sodium methyl cocoyl taurate;
An orally acceptable carrier; and
wherein the oral care composition is free of sodium lauryl sulfate.

2.34 Any of the preceding oral care compositions comprising nitric acid or a water-soluble nitrate salt (e.g., potassium nitrate).

2.35 The preceding oral care composition, wherein the water-soluble nitrate salt is selected from an alkali or alkaline earth metal nitrate, or zinc nitrate, silver nitrate, or ammonium nitrate.

2.36 The preceding oral care composition, wherein the water-soluble nitrate salt is an alkali metal nitrate salt or an alkaline earth metal nitrate salt.

2.37 The preceding oral care composition, wherein the nitrate salt is selected from lithium nitrate, sodium nitrate, potassium nitrate, magnesium nitrate, and calcium nitrate.

2.38 The preceding oral care composition, wherein the nitrate salt is potassium nitrate.

2.39 Any of the preceding oral care compositions, wherein the oral care composition comprises hyaluronic acid (e.g., high-molecular weight hyaluronic acid (HA)) or sodium hyaluronate (e.g., average MW>100,000 Da, e.g., 300 kDa-1 MDa).

The compositions may optionally comprise additional ingredients suitable for use in oral care compositions. The compositions of the disclosure, e.g., any of Composition 1.0 et seq or Composition 2.0 et seq, may be formulated in a suitable dentifrice base, e.g., comprising abrasives, e.g., silica abrasives, surfactants, foaming agents, vitamins, polymers, enzymes, humectants, thickeners, additional antimicrobial agents, preservatives, flavorings, colorings, and/or combinations thereof. Examples of suitable dentifrice bases are known in the art. Alternatively, the compositions may be formulated as a gel (e.g., for use in a tray), chewing gum, lozenge or mint. Examples of suitable additional ingredients that can be employed in the compositions of the present disclosure are discussed in more detail below.

As used herein, an "oral care composition" refers to a composition for which the intended use includes oral care, oral hygiene, and/or oral appearance, or for which the intended method of use comprises administration to the oral cavity, and refers to compositions that are palatable and safe for topical administration to the oral cavity, and for providing a benefit to the teeth and/or oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "orally acceptable" refers to a material that is safe and palatable at the relevant concentrations for use in an oral care formulation, such as a mouthwash or dentifrice.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

Active Agents: The compositions of the disclosure, e.g., any of Composition 1.0 et seq or Composition 2.0 et seq, may comprise various other agents that are active to protect and enhance the strength and integrity of the enamel and tooth structure and/or to reduce bacteria and associated tooth decay and/or gum disease or to provide other desired benefits. Effective concentration of the active ingredients used herein will depend on the particular agent and the delivery system used. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product.

Compositions of the disclosure may contain from 0.1 to 1 wt. % of an antibacterial agent, such as about 0.3 wt. %. Any suitable antimicrobial actives can be employed.

Fluoride Ion Source: The oral care compositions of the disclosure, e.g., any of Composition 1.0 et seq or Composition 2.0 et seq, can comprise one or more additional fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al, the disclosure of each of which is hereby incorporated by reference in their entirety. Representative fluoride ion sources include, but are not limited to, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes sodium fluoride, sodium monofluorophosphate as well as mixtures thereof. In certain embodiments, the oral care composition of the disclosure may contain stannous fluoride and any additional source of fluoride ions or fluorine-providing agents in amounts sufficient to supply, in total, from 25 ppm to 25,000 ppm (mass fraction) of fluoride ions, generally at least 500 ppm, e.g., from 500 to 2000 ppm, e.g., from 1000 to 1600 ppm, e.g., about 1450 ppm. The appropriate level of fluoride will depend on the particular application. A toothpaste for general consumer use would typically have from 1000 to about 1500 ppm, with pediatric toothpaste having somewhat less. A dentifrice or coating for professional application could have as much as 5,000 or even about 25,000 ppm fluoride. Additional fluoride ion sources may be added to the compositions of the disclosure at a level of from 0.01 wt. % to 10 wt. % in one embodiment or from 0.03 wt. % to 5 wt. %, and in another embodiment from 0.1 wt. % to 1 wt. % by weight of the composition. As discussed above, weights of fluoride salts to provide the appropriate level of fluoride ion will vary based on the weight of the counterion in the salt.

Abrasives: The oral care compositions of the disclosure, e.g., any of Composition 1.0 et seq or Composition 2.0 et seq, can comprise abrasives. Examples of suitable abrasives include silica abrasives, such as standard cleaning silicas, high cleaning silicas or any other suitable abrasive silicas. Additional examples of abrasives that can be used in addition to or in place of the silica abrasives include, for example, a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Silica abrasive polishing materials useful herein, as well as the other abrasives, generally have an average particle size ranging between 0.1 and 30 microns, such as between 5 and 15 microns. The silica abrasives can be from precipitated silica or silica gels, such as the silica xerogels described in U.S. Pat. No. 3,538,230, to Pader et al. and U.S. Pat. No. 3,862,307, to Digiulio, the disclosures of which are incorporated herein by reference in their entireties. Particular silica xerogels are marketed under the trade name Syloid® by the W.R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, the disclosure of which is incorporated herein by reference in its entirety. In certain embodiments, abrasive materials useful in the practice of the oral care compositions in accordance with the disclosure include silica gels and precipitated amorphous silica having an oil absorption value of less than 100 cc/100 g silica, such as from 45 cc/100 g to 70 cc/100 g silica.

Oil absorption values are measured using the ASTA Rub-Out Method D281. In certain embodiments, the silicas are colloidal particles having an average particle size of from 3 microns to 12 microns, and from 5 to 10 microns. Examples of low oil absorption silica abrasives useful in the practice of the disclosure are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging from 7 to 10 microns in diameter, and an oil absorption of less than 70 cc/100 g of silica is an example of a low oil absorption silica abrasive useful in the practice of the present disclosure.

Any suitable amount of silica abrasive can be employed. Examples of suitable amounts include 10 wt. % or more dry weight of silica particles, such as from 15 wt. % to 30 wt. % or from 15 wt. % to 25 wt. %, based on the total weight of the composition.

Foaming agents: The oral care compositions of the disclosure, e.g., any of Composition 1.0 et seq or Composition 2.0 et seq, can comprise an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care compositions of the present disclosure. Polyoxyethylene is also commonly known as polyethylene glycol ("PEG") or polyethylene oxide. The polyoxyethylenes suitable for compositions of the present disclosure may have a molecular weight of from 200,000 to 7,000,000. In one embodiment the molecular weight may be from 600,000 to 2,000,000 and in another embodiment from 800,000 to 1,000,000. Polyox® is the trade name for the high molecular weight polyoxyethylene produced by Union Carbide. The foaming agent, (e.g., polyoxyethylene) may be present in an amount of from 0.1% to 50%, in one embodiment from 0.5% to 20% and in another embodiment from 1% to 10%, or from 2% to 5% by weight of the oral care compositions of the present disclosure.

Surfactants: The oral care compositions of the disclosure, e.g., any of Composition 1.0 et seq or Composition 2.0 et seq, can comprise an anionic surfactant that is not sodium lauryl sulfate. For example, in one aspect, any of Composition 1.0 et seq can additionally comprise any of the following surfactants:
  i. water-soluble salts of higher fatty acid monoglyceride monosulfates, such as the sodium salt of the monosulfated monoglyceride of hydrogenated coconut oil fatty acids, sodium cocomonoglyceride sulfate,
  ii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$,
  iii. higher alkyl aryl sulfonates such as sodium dodecyl benzene sulfonate (sodium lauryl benzene sulfonate),
  iv. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In certain embodiments, the anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauroyl sarcosinate and sodium coconut monoglyceride sulfonates are examples of anionic surfactants of this type. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. In one embodiment, the anionic surfactant is present in a toothpaste at from 0.3% to 4.5% by weight, e.g., about 1.5%. The compositions of the disclosure may optionally contain mixtures of surfactants, e.g., comprising anionic surfactants and other surfactants that may be anionic, cationic, zwitterionic or nonionic. Generally, suitable surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al, the disclosures of which are incorporated herein by reference in their entireties.

The surfactant or mixtures of compatible surfactants that are included can be present in the compositions of the present disclosure in from 0.1% to 5.0%, in another embodiment from 0.3% to 3.0% and in another embodiment from 0.5% to 2.0% by weight of the total composition. These ranges do not include the anionic surfactant amounts.

The oral care compositions of the disclosure, e.g., any of Composition 1.0 et seq, can comprise a zwitterionic surfactant, for example a betaine surfactant, for example cocamidopropylbetaine, e.g., in an amount of from 0.1% to 4.5% by weight, e.g., from 0.5 to 2% by weight cocamidopropylbetaine.

Tartar control agents: The oral care compositions of the disclosure, e.g., any of Composition 1.0 et seq or Composition 2.0 et seq, can comprise an anticalculus (tartar control) agent. Suitable anticalculus agents include, without limitation, phosphates and polyphosphates (for example pyrophosphates and tripolyphosphates), polyaminopropanesulfonic acid (AMPS), hexametaphosphate salts, zinc citrate trihydrate, polypeptides, polyolefin sulfonates, polyolefin phosphates, and diphosphonates. The compositions of the disclosure thus may comprise phosphate salts in addition to the zinc phosphate. In particular embodiments, these salts are alkali phosphate salts, e.g., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; and dimeric phosphates such as pyrophosphates; and multimeric phosphates, such as tripolyphosphates, tetraphosphates, hexaphosphates and hexametaphosphates (e.g., sodium hexametaphosphate). In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions may comprise tetrasodium pyrophosphate in an amount of from 0.5 to 5% by weight, e.g., 1-3%, or 1-4%, or 2-4%, or 1-2% or about 2%, or about 4% by weight of the composition. In another embodiment, the compositions may comprise a mixture of tetrasodium pyrophosphate (TSPP) and sodium tripolyphosphate (STPP), e.g., in proportions of TSPP at from 0.5 to 5 wt. %, such as from 1 to 2 wt. % or 1 to 4 wt. % and STPP at from 0.5% to 6 wt. %, such as 1 to 4%, or 2 to 3% by weight of the composition. Such phosphates are provided in an amount effective to reduce erosion of the enamel, to aid in cleaning the teeth, and/or to reduce tartar buildup on the teeth, for example in an amount of from 0.2 to 20 wt. %, e.g., from 1 to 15 wt. %, by weight of the composition.

Flavoring Agents: The oral care compositions of the disclosure, e.g., any of Composition 1.0 et seq or Composition 2.0 et seq, can comprise a flavoring agent. Flavoring agents which are used in the practice of the present disclosure include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of from 0.1 to 5% by weight e.g., from 0.5 to 1.5% by weight.

Polymers: The oral care compositions of the disclosure, e.g., any of Composition 1.0 et seq or Composition 2.0 et seq, can comprise additional polymers to adjust the viscosity of the formulation or enhance the solubility of other ingredients. Such additional polymers include polyethylene glycols, polysaccharides (e.g., cellulose derivatives, for example carboxymethyl cellulose, hydroxymethyl cellulose, ethyl cellulose, microcrystalline cellulose or polysaccharide gums, for example xanthan gum, guar gum or carrageenan gum). Acidic polymers, for example polyacrylate gels, may be provided in the form of their free acids or partially or fully neutralized water soluble alkali metal (e.g., potassium and sodium) or ammonium salts. In one embodiment, the oral care composition may contain PVP. PVP generally refers to a polymer containing vinylpyrrolidone (also referred to as N-vinylpyrrolidone, N-vinyl-2-pyrrolidone and N-vinyl-2-pyrrolidinone) as a monomeric unit. The monomeric unit consists of a polar imide group, four non-polar methylene groups and a non-polar methane group.

In some embodiments, the compositions of the disclosure, e.g., any of Composition 1.0 et seq or Composition 2.0 et seq, can comprise one or more polyethylene glycols, for example, polyethylene glycols in a molecular weight range from 200 to 800. For example, the compositions may comprise one or more of polyethylene glycol 200, polyethylene glycol 300, polyethylene glycol 400, polyethylene glycol, 600 or polyethylene glycol 800.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as a component of the thickening composition to further improve the composition's texture. In certain embodiments, thickening agents in an amount of from 0.5% to 5.0% by weight of the total composition are used.

In some embodiments, the oral care compositions of the disclosure, e.g., any of Composition 1.0 et seq or Composition 2.0 et seq, can comprise an anionic polymer, for example in an amount of from 0.05 to 5%. Examples of such agents generally known for use in dentifrice are disclosed in U.S. Pat. Nos. 5,188,821 and 5,192,531, both of which are incorporated herein by reference in their entirety; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of from 30,000 to 1,000,000, such as from 300,000 to 800,000. These copolymers are available for example as Gantrez, e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to 3% by weight. Other operative polymers include those such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2-methylpropane sulfonic acid having a molecular weight of from 1,000 to 2,000,000. Another useful class of polymeric agents includes polyamino acids containing proportions of anionic surface-active amino acids such as aspartic acid, glutamic acid and phosphoserine, e.g. as disclosed in U.S. Pat. No. 4,866,161, issued to Sikes et al., which is also incorporated herein by reference in its entirety.

In some embodiments, there are no anionic polymers present in the composition. In other embodiments, there may be anionic polymers present, but they do not include copolymers of methyl vinyl ether and maleic acid or anhydride.

Humectants: The oral care compositions of the disclosure, e.g., any of Composition 1.0 et seq or Composition 2.0 et seq, can comprise a humectant. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In one embodiment of the disclosure, the principal humectant is one of glycerin, sorbitol or a combination thereof. The humectant may be present at levels of greater than 15 wt. %, such as from 15 wt. % to 55 wt. %, or from 20 wt. % to 50 wt. %, or from 20 wt. % to 40 wt. %, or about 20% or about 30% or about 40%, based on the total weight of the composition.

Amino Acids: In some aspects, the oral care compositions of the disclosure, e.g., any of Composition 1.0 et seq or Composition 2.0 et seq, can comprise a basic amino acid. The basic amino acids which can be used in the compositions and methods of the disclosure include not only naturally occurring basic amino acids, such as arginine, lysine, and histidine, but also any basic amino acids having a carboxyl group and an amino group in the molecule, which are water-soluble and provide an aqueous solution with a pH of 7 or greater.

For example, basic amino acids include, but are not limited to, arginine, lysine, serine, citrulline, ornithine, creatine, histidine, diaminobutanoic acid, diaminoproprionic acid, salts thereof or combinations thereof. In a particular embodiment, the basic amino acids are selected from arginine, citrulline, and ornithine. In certain embodiments, the basic amino acid is arginine, for example, L-arginine, or a salt thereof.

In another aspect, the compositions of the disclosure (e.g., any of Composition 1.0 et seq or Composition 2.0 et seq) can further comprise one or more neutral amino acid, which can include, but is not limited to, one or more neutral amino acids selected from the group consisting of alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, and combinations thereof.

Other optional ingredients: In addition to the above-described components, the oral care compositions of the disclosure, e.g., any of Composition 1.0 et seq, can comprise a variety of optional oral care ingredients some of which are described below. Optional ingredients include, for example, but are not limited to, adhesives, sudsing agents, flavoring agents, sweetening agents such as sodium saccharin, additional antiplaque agents, abrasives, aesthetics such as $TiO_2$ coated mica or other coloring agents, such as dyes and/or pigments.

In some embodiments, the compositions of the present disclosure, e.g., any of Composition 1.0 et seq or Composition 2.0 et seq, can have any pH suitable for in a product for use in oral care. Examples of suitable pH ranges are from 6 to 9, such as from 6.5 to 8, or 6.5 to 7.5, or about 7.0.

In some embodiments of the disclosure, e.g., any of Composition 1.0 et seq or Composition 2.0 et seq, are either essentially free of, free of, or do not include any sodium hexametaphosphate. In some embodiments, the oral care compositions of the present disclosure are either essentially free of, free of, or do not include any halogenated diphenyl ethers (e.g., triclosan).

In certain aspects the oral care compositions of the disclosure, e.g., any of Composition 1.0 et seq or Composition 2.0 et seq, are either essentially free of, or do not include any sodium lauryl sulfate.

By "essentially free" or "substantially free" it is meant that the compositions have no more than 0.01% by weight of these compounds.

In some embodiments, the compositions of the present disclosure are either essentially free of, free of or do not include any complexing agents for increasing solubility of zinc phosphate. Examples of known complexing agents that can be excluded from the compositions of the present disclosure include the chelating agents taught in U.S. Patent Application No. 2007/0025928, the disclosure of which is hereby incorporated by reference in its entirety. Such chelating agents include mineral surface-active agents, including mineral surface-active agents that are polymeric and/or polyelectrolytes and that are selected from phosphorylated polymers, wherein if the phosphorylated polymer is a polyphosphate, the polyphosphate has average chain length of 3.5 or more, such as 4 or more; polyphosphonates; polycarboxylates; carboxy-substituted polymers; copolymers of phosphate- or phosphonate-containing monomers or polymers with ethylenically unsaturated monomers, amino acids, proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); and mixtures thereof. Other known complexing agents that can be excluded from the compositions of the present disclosure include those taught in CA 2634758, the disclosure of which is incorporated here by reference in its entirety. Examples include polyphosphorylated inositol compounds such as phytic acid, myo-inositol pentakis(dihydrogen phosphate); myo-inositol tetrakis(dihydrogen phosphate), myo-inositol trikis(dihydrogen phosphate), and alkali metal, alkaline earth metal or ammonium salts of any of the above inositol compounds. Phytic acid is also known as myo-inositol 1,2,3,4,5,6-hexakis (dihydrogen phosphate) or inositol hexaphosphoric acid.

In some embodiments, the compositions of the disclosure (e.g., any of Composition 1.0 et seq or Composition 2.0 et seq) can comprise a non-ionic block copolymer, optionally together with an alkyl glucoside. The non-ionic block copolymer may be a poly(propylene oxide)/poly(ethylene oxide) copolymer. In some embodiments, the copolymer has a polyoxypropylene molecular mass of from 3000 to 5000 g/mol and a polyoxyethylene content of from 60 to 80 mol %. In some embodiments, the non-ionic block copolymer is a poloxamer. In some embodiments, the non-ionic block copolymer is selected from: Poloxamer 338, Poloxamer 407, Poloxamer, 237, Poloxamer, 217, Poloxamer 124, Poloxamer 184, Poloxamer 185, and a combination of two or more thereof. In some embodiments, the copolymer is Poloxamer 407. In some embodiments, the compositions of the disclosure (e.g., any of Composition 1.0 et seq) can comprise a betaine amphoteric surfactant and a non-ionic block copolymer, optionally together with an alkyl glucoside.

The compositions of the disclosure (e.g., any of Composition 1.0 et seq or Composition 2.0 et seq) are intended for topical use in the mouth and so salts for use in the present disclosure should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In another aspect, the present disclosure provides a method of treatment or prevention of erosive tooth demineralization, repair of enamel, gingivitis, plaque, and/or dental caries, the method comprising the application to the oral cavity of a person in need thereof a composition according to the disclosure (e.g., any of Composition 1.0 et seq or Composition 2.0 et seq), e.g., by brushing, for example, one or more times per day.

In one aspect, the present disclosure provides a method of treatment or prophylaxis for improved repair of acid softened enamel in the oral cavity of a person in need thereof, wherein the method comprises administering a composition according to the disclosure (e.g., any of Composition 1.0 et seq or Composition 2.0 et seq) to the oral cavity of the person in need thereof, e.g., by brushing, for example, one or more times per day.

In another aspect, the present disclosure provides a method of using the compositions described herein (e.g., any of Compositions 1.0 et seq) to treat, reduce or control the incidence of enamel erosion. The methods comprise applying any of the compositions as described herein to the teeth, e.g., by brushing, or otherwise administering the compositions to the oral cavity of a subject in need thereof. The compositions can be administered regularly, such as, for example, one or more times per day. In various embodiments, administering the compositions of the present disclosure to a patient can provide one or more of the following benefits: (i) reduce hypersensitivity of the teeth, (ii) reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) increase relative levels of non-cariogenic and/or non-plaque forming bacteria, (ix) reduce or inhibit formation of dental caries, (x) reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues. The disclosure further provides compositions for use in any of the above methods. Further embodiments provide methods wherein at least one tooth is remineralized after administration of a composition as described herein.

In yet another aspect, the compositions disclosed herein (e.g., any of Compositions 1.0 et seq or Composition 2.0 et seq) provide improved repair of acid softened enamel. For example the compositions disclosed herein (e.g., any of Compositions 1.0 et seq or Composition 2.0 et seq) can be administered, to a subject in need thereof, as part of a method to increase strength or hardness of damaged and/or softened enamel. In another aspect, the compositions disclosed herein (e.g., any of Compositions 1.0 et seq or Composition 2.0 et seq) can be administered, to a subject in need thereof, as part of a method to promote remineralization of enamel.

The present application further discloses a method of making any of the compositions of the present disclosure, e.g., any of Composition 1.0 et seq or Composition 2.0 et seq.

EXAMPLES

Example 1—Dentifrice Formulation

In one aspect, representative dentifrice formulations according to the present disclosure are prepared according to Table 1 below:

TABLE 1

| Ingredients | Weight % |
| --- | --- |
| Water | Q.S. (e.g., 15-40) |
| Humectants | 15%-50% (e.g., 35%) |
| Polymers | 0.5%-5% (e.g., 1.4%) |
| Abrasives | 10%-25% (e.g., 15%) |
| Thickeners | 1%-10% (e.g., about 6%) |
| Zinc Citrate | 0.1%-5% (e.g., 0.5%) |
| Zinc Oxide | 0.1%-5% (e.g., 1%) |
| L-Arginine | 0.1-5 (e.g., 1.5) |
| Flavor, Sweetener, Colors | 1-5% (e.g., 2.5%) |
| Alkali Phosphate Salts | 0.1%-2% (e.g., 0.5%) |
| Sodium Methyl Cocoyl Taurate | 0.01-10 (e.g., 2.5%) |
| Cocamidopropyl Betaine (30% solution) | 0.1-5 (e.g., 3%) |
| Sodium Fluoride | 0.1%-0.8% (e.g., 0.32%) |
| Preservative | 0.1%-1% (e.g., 0.4%) |
| pH adjuster | 0.1%-1% (e.g., 0.35%) |
| Total Components | 100.0% |

Example 2—Enamel Repair Assay

Compositions detailed in Table 2 below are studied for their ability to repair enamel in laboratory tests:

TABLE 2

| Ingredients | Formula A (% by wt.) | Formula B (% by wt.) | Formula C (% by wt.) | Formula D (% by wt.) |
| --- | --- | --- | --- | --- |
| Water | q.s. | q.s. | q.s. | q.s. |
| Humectants | 35% | 35% | 35% | 35% |
| Polymers | 1.4% | 1.4% | 1.4% | 1.4% |
| Abrasives | 15% | 15% | 15% | 15% |
| Thickeners | 6% | 6% | 6% | 6% |
| Zinc Citrate | 0.5% | 0.5% | 0.5% | 0.5% |
| Zinc Oxide | 1% | 1% | 1% | 1% |
| L-Arginine | 1.5% | 1.5% | 1.5% | 1.5% |
| Flavor, Sweetener, Colors | 2.55% | 2.55% | 2.55% | 2.55% |
| Alkali Phosphate Salts | 0.5% | 0.5% | 0.5% | 0.5% |
| Sodium Methyl Cocoyl Taurate | — | — | — | 2.5% |
| Cocamidopropyl Betaine (30% solution) | 1.25% | 3% | 3% | 3% |
| Non-Ionic Block Copolymer | 0.5% | — | — | — |
| Sodium Fluoride | 0.32% | 0.32% | 0.32% | 0.32% |
| Preservative | 0.4% | 0.4% | 0.4% | 0.4% |
| 85% Syrupy phosphoric acid | 0.35% | 0.35% | 0.35% | 0.35% |
| Sodium Lauryl Sulfate | 2% | — | — | — |
| Sodium Cocoyl Glutamate | — | 2.5% | — | — |
| Lauryl Glucoside | — | 2.5% | — | — |
| Sodium Lauryl Sarcosinate (e.g., Maprosyl ® 30-B) | — | — | 6.67% | — |
| Total Components | 100% | 100% | 100% | 100% |

Formulas A, B, C and D above are tested via the following procedure and analyzed for their respective ability to repair acid damaged enamel in vitro. The experimental procedure is as follows:

Polished bovine enamel blocks are dried overnight and baseline surface hardness is measured for each block. Only blocks with Knoops Hardness larger than 300 are selected (KHN>300, 50 g force) for the in vitro study.

Each block is then submerged into 2 ml of demineralization solution (1% citric acid pH adjusted to 3.5 with NaOH) for 10 minutes in a 24 well plate.

Each block is then rinsed twice with 8 ml of deionized (DI) water using 6 well plates at 300 rpm shaking for 2 minutes, and let to dry overnight.

The surface hardness post-acid challenge is measured again. Only blocks with more than 40% hardness lost are selected. A total of 20 selected blocks are prepared, randomized and grouped into the 4 treatments (n=5).

Each group of blocks are then submerged into 2 ml of respective toothpaste slurry (1 part toothpaste: 2 part DI water) for 2 minutes at 100 rpm shaking.

Enamel blocks are rinsed twice with 8 ml of DI water (per block) using 6 well plates at 300 rpm shaking for 2 minutes.

Blocks are submerged into remineralization (remin) solution (0.2205 g/L $CaCl_2*2H_2O$, 0.1225 g/L $KH_2PO_4$, 9.6915 g/L KCl and 4.766 g/L HEPEs buffer) for 4 hours.

Steps 6 and 7 are repeated again and blocks are then submerged into remin solution overnight (>16 hrs)

Next day, each block is rinsed once with 8 ml of DI water using a 6 well plate at 300 rpm shaking for 2 minutes.

Blocks are allowed to dry overnight and final surface hardness is measured.

% of repair calculation is calculated by:

$$\% \text{ Hardness Repair} = \frac{\text{Final Hardness} - \text{Etched Hardness}}{\text{Sound Hardness} - \text{Etched Hardness}} \times 100\%$$

One way ANOVA method is applied for statistical analysis.

TABLE 3

Enamel Repair Efficacy of Respective Toothpaste Treatments **

| Formula | N | % Repair (mean) | Grouping* |
|---|---|---|---|
| Formula A | 5 | 12.81 | B |
| Formula B | 3 | 13.12 | B |
| Formula C | 5 | 23.70 | AB |
| Formula D | 5 | 32.69 | A |

*Means that do not share a letter are significantly different
** One-Way ANOVA and grouping information using the Tukey method and 95% confidence.

As demonstrated in Table 3, the change of surfactant system has an impact on the efficacy of toothpaste formulations in repairing acid damaged enamel. The sodium methyl cocoyl taurate and cocamidopropyl betaine surfactant combination (Formula D) repair enamel significantly better than Formula A which contains sodium lauryl sulfate and cocamidopropyl betaine. Formula D also demonstrates an improved trend over other anionic surfactants, e.g., sodium lauryl sarconsinate as evidenced by a comparison with the results of Formula C. Accordingly, the surfactant combination of sodium methyl cocoyl taurate is recommended to optimize efficacy for repair acid damaged enamel.

While the disclosure has been described with respect to specific examples including presently preferred modes of carrying out the disclosure, those skilled in the art will appreciate that there are numerous variations and permutations of the above-described systems and techniques. It is to be understood that other embodiments may be utilized and structural and functional modifications may be made without departing from the scope of the present disclosure.

The invention claimed is:

1. An oral care composition comprising:
    a source of zinc ions comprising zinc citrate and zinc oxide, wherein the zinc citrate is in an amount from 0.25% to 1.0% by wt. and zinc oxide is present in an amount of from 0.75% to 1.25% by wt. based on the weight of the oral care composition,
    a source of fluoride, wherein the source of fluoride comprises sodium fluoride in an amount from 0.2% to 2% by weight, relative to the weight of the oral care composition;
    an effective amount of a zwitterionic surfactant, wherein the zwitterionic surfactant comprises cocamidopropyl betaine in an amount from 0.5%-5% by wt. of the composition; and
    an effective amount of a taurate surfactant, wherein the taurate surfactant comprises sodium methyl cocoyl taurate in an amount from 0.25% to 5% by weight of the composition.

2. The oral care composition of claim 1 comprising an amino acid, wherein the amino acid is a basic amino acid.

3. The oral care composition of claim 2, wherein the basic amino acid comprises arginine or lysine, and wherein the arginine or lysine is present in an amount corresponding to 1% to 15% by wt., wherein the weight of the basic amino acid is calculated as free form.

4. The oral care composition of claim 1, wherein the composition comprises:
    Zinc oxide from 0.75%-1.25% by wt.;
    Zinc citrate from 0.25%-0.75% by wt.;
    Arginine from 0.5%-3% by wt.;
    Sodium fluoride from 0.2% to 2% by weight;
    Sodium methyl cocoyl taurate from 0.5%-4% by wt.;
    Cocamidopropyl Betaine from 0.5%-5% by wt.; and
    An orally acceptable carrier.

5. A method of treatment or prevention of erosive tooth demineralization, gingivitis, plaque, and/or dental caries, the method comprising the application to the oral cavity of a person in need thereof the oral care composition according to claim 1.

6. The oral care composition of claim 1, wherein the oral care composition comprises water in the amount of 10%-50% by wt., relative to the weight of the oral care composition.

7. The oral care composition of claim 1, wherein zinc citrate is present in an amount of about 0.5% by wt.

8. The oral care composition of claim 1, wherein the zinc oxide is present in an amount of about 1.0% by wt.

9. The oral care composition of claim 1, wherein the zinc citrate is present in an amount of about 0.5% by wt. and zinc oxide is present in an amount of about 1.0% by wt.

10. The oral care composition of claim 1, wherein the composition comprises hyaluronic acid.

11. The oral care composition of claim 1, wherein the composition comprises potassium nitrate.

12. The oral care composition of claim 1, wherein the composition is free of sodium lauryl sulfate.

13. The oral care composition of claim 1, wherein the cocamidopropyl betaine is present in an amount of about 0.9% by wt. of the composition.

14. A method of treatment or prophylaxis for improved repair of acid softened enamel in the oral cavity of a person in need thereof, wherein the method comprises administering a composition according to claim 1 to the oral cavity of the person in need thereof.

* * * * *